United States Patent
Demers

(10) Patent No.: US 7,094,609 B2
(45) Date of Patent: Aug. 22, 2006

(54) SPATIALLY ADDRESSABLE COMBINATORIAL CHEMICAL ARRAYS IN ENCODED OPTICAL DISK FORMAT

(75) Inventor: James Paul Demers, New York, NY (US)

(73) Assignees: Burstein Technologies, Inc., Irvine, CA (US); Nagaoka & Co. Ltd., Hyogo (JP)

(*) Notice: Subject to any disclaimer, the term of this patent is extended or adjusted under 35 U.S.C. 154(b) by 0 days.

(21) Appl. No.: 09/269,092

(22) PCT Filed: Sep. 19, 1997

(86) PCT No.: PCT/US97/16738

§ 371 (c)(1),
(2), (4) Date: Mar. 18, 1999

(87) PCT Pub. No.: WO98/12559

PCT Pub. Date: Mar. 26, 1998

(65) Prior Publication Data

US 2002/0058242 A1 May 16, 2002

Related U.S. Application Data

(60) Provisional application No. 60/026,415, filed on Sep. 20, 1996.

(51) Int. Cl.
*C12Q 1/68* (2006.01)
*A61K 38/00* (2006.01)
*C07H 28/00* (2006.01)

(52) U.S. Cl. .................. 436/518; 435/6; 435/DIG. 43; 435/DIG. 44; 435/DIG. 45; 530/333; 530/334; 536/25.3; 235/454

(58) Field of Classification Search ................ 436/518, 436/501, 45, 164, 165; 435/6, DIG. 43, DIG. 44, 435/DIG. 45, 4, 7.1, DIG. 49, DIG. 22, DIG. 34, 435/DIG. 2; 530/333, 334; 536/25.3; 235/454
See application file for complete search history.

(56) References Cited

U.S. PATENT DOCUMENTS

| | | | |
|---|---|---|---|
| 4,194,304 A | 3/1980 | Wolcott | 35/25 |
| 4,719,615 A | 1/1988 | Feyrer et al. | 369/284 |
| 4,886,589 A | 12/1989 | Southern | 204/182.8 |
| 4,927,766 A | 5/1990 | Auerbach et al. | 436/44 |
| 5,002,867 A | 3/1991 | Macevicz | 435/6 |
| 5,119,363 A | 6/1992 | Satoh et al. | |
| 5,143,854 A * | 9/1992 | Pirung et al. | |
| 5,173,262 A | 12/1992 | Burtis et al. | |
| 5,202,231 A | 4/1993 | Drmanac et al. | 435/6 |
| 5,318,679 A | 6/1994 | Nishioka | 204/157.68 |
| 5,329,461 A | 7/1994 | Allen et al. | |
| 5,405,783 A | 4/1995 | Pirung et al. | 436/518 |
| 5,407,554 A | 4/1995 | Saurer | |
| 5,412,087 A | 5/1995 | McGall et al. | 536/24.3 |

(Continued)

FOREIGN PATENT DOCUMENTS

| | | |
|---|---|---|
| EP | 0 392 475 | 10/1990 |
| EP | 0 417 305 | 3/1991 |
| EP | 0 504 432 | 9/1992 |
| EP | 0 521 421 | 1/1993 |
| EP | 0 703 825 | 7/1997 |
| GB | 2 337 113 A | 11/1999 |
| WO | WO 96/09548 | 3/1996 |
| WO | WO 97/21090 | 6/1997 |
| WO | WO 97/41256 | 11/1997 |
| WO | WO 98/12559 | 3/1998 |
| WO | WO 98/38510 | 9/1998 |
| WO | WO 00/05582 | 2/2000 |
| WO | WO 00/26677 | 5/2000 |

OTHER PUBLICATIONS

US 5,382,513, 1/1995, Lam et al. (withdrawn)
Laser Scanner Method for Determining Number and Size of Particles by Frank Zitco et al., published May 4, 1993 as United States Statutory Invention Regulation No. H1183; pp. 1–15.
Bell, "Next–Generation Compact Discs," *Scientific American*, pp. 42–46 (Jul. 1996).
Blanchard et al., "Sequence to Array: Probing the genome's secrets," *Nature Biotrechnology*, 14:1649 (Dec. 1996).
Brecht et al., "Transducer–Based Approaches for Parallel Binding Assays in HTS," *J. Biomolecular Screening*, 1(4):191–201 (1996).
Catalogue entry, "Laser Microbeam Irradiation System," Laser Science, Inc. date unknown.
Catalogue entry, "High Power Nitrogen Laser," Laser Science, Inc. (May, 1995).
Catalogue entry, "Low Cost, Sealed, Compact UV & Visible Lasers," Laser Science, Inc. date unknown.
Chee et al., "Accessing Genetic Information with High–Density DNA Arrays," *Science*, 274:610–614 (Oct. 25, 1996).
Chigita et al., "How CD–Recordable and CD–Rewritable Dyes Work," The CD Information Center (Jun. 30, 1996).
Clark, "Materials for Optical Storage," *Chemistry & Industry*, pp. 258–263 (Apr. 15, 1985).
Ferguson et al., "A fiber–optic DNA Biosensor microarray for the analysis of gene expression," *Nature Biotechnology*, 14: 1681–1684 (Dec. 1991).
Fodor et al., "Light–directed, spatially addressable parallel chemical synthesis," *Science*, 251(4995):767–73 (1991).
Fodor et al., "Accessing Genetic Information with DNA Arrays," (abstract for Nov. 1994 DOE Human Genome Program Contractor–Grantee Workshop).

(Continued)

*Primary Examiner*—Padmashri Ponnaluri
(74) *Attorney, Agent, or Firm*—Knobbe, Martens, Olson & Bear, LLP

(57) ABSTRACT

A method for preparing very large spatially-addressable arrays of chemical compounds by light-directed synthesis is provided, wherein the light is provided by a laser and the compounds are arrayed on a rotating disc in a CD-ROM format. A method for assaying the resulting array with a CD-ROM mechanism is also provided.

9 Claims, No Drawings

U.S. PATENT DOCUMENTS

| | | |
|---|---|---|
| 5,413,939 A | 5/1995 | Gustafson et al. .......... 436/518 |
| 5,424,186 A | 6/1995 | Fodor et al. ................... 435/6 |
| 5,429,807 A | 7/1995 | Matson et al. .............. 422/131 |
| 5,436,327 A | 7/1995 | Southern et al. ......... 536/25.34 |
| 5,445,934 A | 8/1995 | Fodor et al. ................... 435/6 |
| 5,449,754 A | 9/1995 | Nishioka .................... 530/334 |
| 5,453,969 A | 9/1995 | Psaltis et al. ............... 369/109 |
| 5,457,582 A | 10/1995 | Victoria ....................... 360/59 |
| 5,463,564 A | 10/1995 | Agrafiotis et al. .......... 364/496 |
| 5,471,455 A | 11/1995 | Jabr ........................... 369/107 |
| 5,486,633 A | 1/1996 | Pirrung et al. .............. 556/410 |
| 5,488,567 A | 1/1996 | Allen et al. |
| 5,489,678 A | 2/1996 | Fodor et al. ............... 536/22.1 |
| 5,492,806 A | 2/1996 | Drmanac et al. .............. 435/5 |
| 5,497,367 A | 3/1996 | Yamagami et al. ...... 369/275.2 |
| 5,510,270 A | 4/1996 | Fodor et al. ................ 436/518 |
| 5,513,169 A | 4/1996 | Fite et al. |
| 5,525,464 A | 6/1996 | Drmanac et al. .............. 435/6 |
| 5,527,681 A | 6/1996 | Holmes ......................... 435/6 |
| 5,536,548 A | 7/1996 | Koji et al. ................. 428/64.1 |
| 5,556,752 A | 9/1996 | Lockhart et al. ............... 435/6 |
| 5,578,832 A | 11/1996 | Trulson et al. ........... 250/458.1 |
| 5,593,839 A | 1/1997 | Hubbell et al. ................ 435/6 |
| 5,599,695 A | 2/1997 | Pease et al. ............... 435/91.1 |
| 5,631,734 A | 5/1997 | Stern et al. .................. 356/317 |
| 5,631,844 A | 5/1997 | Margrey et al. |
| 5,654,413 A | 8/1997 | Brenner ..................... 536/22.1 |
| 5,667,667 A | 9/1997 | Southern .................... 205/687 |
| 5,695,934 A | 12/1997 | Brenner ......................... 435/6 |
| 5,695,940 A | 12/1997 | Drmanac et al. .............. 435/6 |
| 5,700,637 A | 12/1997 | Southern ....................... 435/6 |
| 5,710,000 A | 1/1998 | Sapolsky et al. .............. 435/6 |
| 5,733,729 A | 3/1998 | Lipshutz et al. ............... 435/6 |
| 5,737,478 A | 4/1998 | Yamagishi et al. |
| 5,744,305 A | 4/1998 | Fodor et al. ................... 435/6 |
| 5,753,788 A | 5/1998 | Fodor et al. ............... 536/22.1 |
| 5,770,367 A | 6/1998 | Southern et al. ............... 435/6 |
| 5,770,456 A | 6/1998 | Holmes ...................... 436/518 |
| 5,770,722 A | 6/1998 | Lockhart et al. ........... 536/25.3 |
| 5,793,969 A | 8/1998 | Kamentsky et al. |
| 5,795,716 A | 8/1998 | Chee .............................. 435/6 |
| 5,800,992 A | 9/1998 | Fodor et al. ................... 435/6 |
| 5,831,070 A | 11/1998 | Pease et al. ............... 536/25.3 |
| 5,834,758 A | 11/1998 | Trulson et al. ........... 250/201.2 |
| 5,837,552 A | 11/1998 | Cotton et al. |
| 5,837,832 A | 11/1998 | Chee et al. ................. 536/22.1 |
| 5,843,655 A | 12/1998 | McGall .......................... 435/6 |
| 5,856,101 A | 1/1999 | Hubbell .......................... 435/6 |
| 5,856,104 A | 1/1999 | Chee et al. ..................... 435/6 |
| 5,856,174 A | 1/1999 | Lipshutz et al. ......... 435/286.5 |
| 5,858,659 A | 1/1999 | Sapolsky et al. .............. 435/6 |
| 5,861,242 A | 1/1999 | Chee et al. ..................... 435/5 |
| 5,863,708 A | 1/1999 | Zanzucchi et al. |
| 5,874,219 A | 2/1999 | Rava et al. ..................... 435/6 |
| 5,878,018 A | 3/1999 | Moriya et al. |
| 5,879,774 A | 3/1999 | Taylor et al. |
| 5,882,930 A | 3/1999 | Bajier .......................... 436/49 |
| 5,892,577 A | 4/1999 | Gordon ........................ 356/73 |
| 5,922,617 A | 7/1999 | Wang et al. |
| 5,994,150 A | 11/1999 | Challener et al. |
| 6,030,581 A | 2/2000 | Virtanen |
| 6,121,048 A * | 9/2000 | Zaffaroni et al. |
| 6,327,031 B1 | 12/2001 | Gordon |
| 6,342,395 B1 | 1/2002 | Hammock et al. |
| 2002/0097658 A1 | 7/2002 | Worthington |

OTHER PUBLICATIONS

Frank et al., "Structure in Thin and Ultrathin Spin–Cast Polymer Films," *Science*, 273:912–915 (Aug. 16, 1996).
Freemantle, Michael, "Photochemical Strategy Patterns Nanoparticles," *C&EN* (May 26, 1997).
Gette et al., "Precision Scanning Technology for Complex Genetic Analysis," *American Laboratory*, pp. 15–17 (Mar., 1997).
Goffeau, "Molecular Fish on Chips," *Nature*, 385:202–203 (Jan. 16, 1997).
Guglielmetti, "4n+2 Systems: Spiropyrans", in *Photochromism: Molecules and Systems*, Heinz Dürr and Henri Bouas–Laurent (eds.), Elsevier (1990), pp. 314–466 (1990).
Gunshor et al., "Blue–Laser CD Technology," *Scientific American*, pp. 48–51 (Jul. 1996).
Jolley, "Fluorescence Polarization Assays for the Detectin of Porteases and Their Inhibitors," *J. Biomol. Screening*, 1:33–38 (1996).
Jung et al., "Multiple Peptide Synthesis Methods and Their Applications," *Angewandte Chemie Int. English Ed.*, 31(4): 367–486 (1992).
Konings et al., "Deconvoluation of Combinatorial Libraries for Drug Discovery: Theoretical Comparison of Pooling Strategies," *J. Med. Chem.*, 39:2710–2719 (1996).
Lockhart et al., "Expression monitoring by hybridization to high–density oligonucleotide arrays," *Nature Biotechnology*, Dec. 1996, vol. 14:1675–1680 (Dec. 1996).
Mandenius et al., "Reversible and Specific Interaction of Dehydrogenases with a Coenzyme–Coated Surface Continuously Monitored with a Reflectometer," *Anal. Biochem.*, 157:283–288 (1986).
Mandenius et al., "interaction of proteins and cells with affinity ligands covalently coupled to silicon surfaces as monitored by ellipsometry," *Anal. Biochem.*, 137:106–114 (1984).
Myshko, "The cause, the cure," *R&D Directions*, pp. 16–22 (Jul./Aug. 1997).
Pease et al., "Light–generated Oligonucleotide Arrays for Rapid DNA Sequence, Analysis," *Proc. Natl. Acad. Sci. USA*, 91:5022–5026 (May 1994).
Pennisi, "From Genes to Genome Biology," *Science*, 272:1736–1738 (1996).
Pillai, "Photoremovable Protecting Groups in Organic Synthesis," *Synthesis*, 1980(1):1–26 (1980).
Pirrung et al., "Comparison of Methods for Photochemical Phosphoramidite–Based DNA Synthesis", *J. Org. Chem.*, 60:6270 (1995).
Rawal et al., "Thermolytic Removal of t–Butyloxycarbonyl (BOC) Protecting Group on Indoles and Pyrrholes," *Tetrahedron Lett.*, 26:6141–6142 (1985).
Vossmeyer, "Light–Directed Assembly of Nanoparticles," *Angew. Chem. Int. Ed. Engl.*, 6:1080–1083 (1997).
Wasserman et al., "The Use of β–Lactams in the Synthesis of Spermine and Spermidine Alkaloids: Total Synthesis of Homaline", *Tetrahedron*, 39:2459–2464 (1983).
Wilson–Lingaro et al., "Deconvolution and Combinatorial Libraries for Drug Discovery: Experimental Comparison of Pooling Strategies," *J. Med. Chem.*, 39:2720–2726 (1996).
Zambounis et al., "Latent Pigments Activated by Heat," *Nature*, 388:131–132 (Jul. 10, 1997).
Zehavi, "Applications of Photosensitive Protecting Groups in Carbohydrate Chemistry," in *Advances in Carbohydrate Chemistry & Biochemistry*, vol. 46, pp. 179–204 (1988).

* cited by examiner

SPATIALLY ADDRESSABLE COMBINATORIAL CHEMICAL ARRAYS IN ENCODED OPTICAL DISK FORMAT

This is a 371 of PCT/US97/16738 which was filed on September 19, 1997, and which claims the priority of provisional application Ser. No. 60/026,415 filed Sep. 20, 1996.

FIELD OF THE INVENTION

The invention has applications in the fields of chemistry, drug discovery, and genomics. The invention relates to: (1) methods for conducting chemical reactions on a support surface with spatial selectivity; (2) the spatially-addressable arrays of compounds (chemical libraries) produced thereby; and (3) methods for detecting specific members of these arrays of compounds, including methods of assaying for the specific binding of substances such as receptors, antibodies or other ligands, as well as methods of assaying for biological activity or other desirable property. The invention employs laser light under computer control for both the synthesis and assay of the arrays, using recordable compact-disc technology previously developed for optical storage of computer data.

BACKGROUND OF THE INVENTION

The advantages of combinatorial chemistry for the rapid generation of chemical compounds for pharmaceutical screening are well established. The single greatest strength of combinatorial chemistry is that it makes possible the generation of libraries of huge numbers of compounds in a relatively short period of time.

Several methods have been employed for the preparation of such libraries, e.g., solution-phase synthesis; solid-phase synthesis on polymer beads or other divided supports; synthesis on soluble, precipitatable polymer supports; and synthesis on planar supports. All of these methods are capable of generating large libraries (i.e., libraries containing a large number of compounds), but none of them are amenable to rapid screening of the libraries for binding activity, biological activity, or other desirable properties.

Current methods for screening libraries include those in which individual library members, or small groups of members, are assayed in microtiter plates, e.g., by screening for a desired activity or for binding to a specific binding partner, such as a receptor or antibody or other ligand, but the number of compounds that can be assayed at once is on the order of $10^2$ to $10^4$: one compound per well in a 96-well microtiter plate screens at most 96 compounds, while twenty compounds per well in a 384-well plate screens about 7680 compounds. The latter approach, while permitting higher throughput, requires secondary screening to identify the active species in any given well. For example, screening a library containing all of the 3.2 million possible pentapeptides which could be made from the twenty natural amino acids (i.e., a 3.2-million-member library) by these methods would require 500 to 3400 plates. Screening a library of the 64 million possible hexapeptides would require 10,000 to 68,000 plates. Robotic systems are available for microtiter plate assays, but screening a large library by such a method remains a massive undertaking. Furthermore, in a pharmaceutical discovery environment this represents only one of the many assays an organization might wish to conduct.

An alternative to testing individual compounds is the testing of complex mixtures, with various "deconvolution" strategies being employed to deduce the active species. These strategies have in common the re-synthesis and re-testing of successively less-complex mixtures. In addition to the great effort involved, the testing of complex mixtures is limited by the low concentration of any individual species in the mixture, and is susceptible to false positive results from the additive effects of large numbers of weakly active species. In practice, deconvolution has had limited success in probing large libraries of compounds. See L. Wilson-Lingaro, J. Med. Chem., 39, 2720–2726 (1996); and D. A. M. Konings, J. Med. Chem., 39, 2710–2719 (1996), and references therein, for a discussion of deconvolution strategies.

Ideally, the probing of a combinatorial library would be conducted in a single operation, with the active members of the library being in some way "pointed out" of the vast population of compounds by the assay. Two of the current methods meet this requirement. Both methods employ solid-phase synthesis, and both require that the library members remain attached to the solid support. In one method, a library of compounds bound to polystyrene beads is prepared by the split-mix method. The library is assayed in a single batch, by being exposed to a molecule of interest, such as a receptor, enzyme, or other specific binding partner. Any beads to which the molecule binds are visualized (e.g., by a colorimetric assay), and beads so identified are selected and the structure of the library member attached to the bead is determined. This can be done by sequencing if the compound is a peptide or nucleic acid, as described, e.g., in U.S. Pat. No. 5,382,513 (incorporated herein by reference). The structure of the compound on the bead may in some cases be deduced from spectroscopic evidence (see, e.g., U.S. Pat. No. 5,382,513), or by decoding a chemical tag that reveals the chemical history of the bead, as described in patent application WO 95/24186 (incorporated herein by reference). The method is in principle capable of screening very large libraries, limited only by the number of beads one is willing to examine. In practice, libraries of $10^4$ to $10^6$ members can be dealt with in this fashion.

The second approach involves physically locating a compound or compounds in a spatially addressable array of compounds on a planar support. In this approach, a compound's identity is revealed by its location in the array. One method of this type employs an array of compounds generated by light-directed synthesis, as first disclosed by Fodor et al. in Science, 251, 767–773 (1991), in which a fraction of sites on a planar support carrying photo-detachable protecting groups is exposed to light through a photolithographic mask, and the fraction of sites thus deprotected are functionalized with a specific monomer or building block, itself carrying a photo-detachable protecting group. The process is repeated with the mask in a different position or orientation, or with a different mask, and a second monomer or building block is attached to the support and/or to the first monomer residues. After numerous such cycles, with careful attention to the pattern of masking, an array of compounds is built up on the support. The final array is completely deprotected, and exposed to the ligand of interest. Binding of the ligand is visualized by immunofluorescence, using antibodies against the ligand which are tagged with a fluorescent dye. Under a fluorescence microscope, any location in the array to which the ligand has bound is visible as a fluorescent area, and the x-y coordinates of the area reveals the identity of the library member to which the ligand was bound. This technology, as applied to polypeptide and oligonuceotide synthesis, is known as Very Large Scale Immobilized Polymer Synthesis, or VLSIPS. It is described in U.S. Pat. Nos. 5,143,854, 5,413,939, 5,424,186, and 5,527,681, all of which are incorporated herein by reference.

The photolithographic method of synthesis, however, is cumbersome, and requires a substantial investment in very specialized equipment. A further investment in a fluorescence microscope or a specialized scanner is required for the assay, and highly skilled technicians are required, at least to conduct the synthesis aspect of the process. The scale of library synthesis is limited by the size of the masks and by the translational reach of the scanning device, which together limit the accessible surface for synthesis to a few square centimeters. In practice this technique is presently limited to arrays of $10^4$ to $10^5$ compounds. For these reasons the method is not routinely employed; see G. Jung and A. G. Beck Sickinger in *Angewandte Chemie*, 31, 367 (1992).

As an alternative to photolithography, the use of directed laser light to conduct light-directed synthesis has been described in U.S. Pat. Nos. 4,719,615 and 5,318,679 (both of which are incorporated herein by reference). In the latter patent, a rectangular array support is either held stationary or translated, while a laser beam is scanned across the array by means of a rotating mirror, in the manner of an ordinary laser printer. This provides an alternative to the photolithographic masking approach, but fluorescence microscopy is still relied upon as an assay method.

Another alternative method for the synthesis of spatially addressable arrays utilizes ink-jet printing technology to spray micro-droplets of reagent solutions onto a substrate. This method is disclosed in U.S. Pat. Nos. 5,474,796 and 5,449,754, both of which are incorporated herein by reference. This method is in theory capable of preparing arrays of $10^7$ compounds, but a method of indexing such large arrays is not disclosed. Again, fluorescence microscopy is the preferred means of conducting an assay.

There remains a need for reliable methods of generating very large, very high-density arrays of chemical compounds, on the order of about $10^8$ or more compounds, along with a method of rapidly screening such arrays for chemical properties of interest, such as binding to antibodies, cellular receptors or other ligands, catalytic activity, or inhibition of enzymes.

BRIEF DESCRIPTION OF THE INVENTION

The present invention provides an alternative method of preparing and assaying a spatially addressable array of compounds on a planar support. By the method of the present invention, light-directed synthesis is carried out using laser light, but with the advantage that the synthesis support is in the form of a spinning disc. The ability of modern mechanical-optical systems to direct laser light to very small areas with very high precision makes it possible to selectively and reproducibly irradiate over $10^9$ individual locations on a single 5.5-inch disc, as is done for example when reading a CD-ROM. Thus, even with ten-fold redundancy to allow for statistical errors and noise, light-directed synthesis with laser light in the CD-ROM format might enable the preparation of arrays (referred to herein as CD-arrays) of over $10^8$ compounds on a single support disc.

In the present invention, a disc-shaped CD-array, functionalized on its surface with reactive groups which are blocked by laser-removable protecting groups, is rotated under a laser beam which is scanned radially across the disc. The radial position of the laser beam, the angular position of the disc, and the on/off status of the laser are all under the control of a computer, which "writes" to the disc in the usual fashion. Wherever the CD-array is "written to", i.e. irradiated, the protecting groups are removed, activating "synthesis sites" where chemical reactions can be carried out. These synthesis sites, arranged in annular or spiral tracks, correspond to the "pits" encoding digital information on a conventional CD-ROM. Recordable CD-ROM drives capable of carrying out most of the mechanical aspects of the present invention are commercially available.

The term "CD-array" as used herein should be understood to refer to any circular disc bearing synthesis sites or synthetic molecules arrayed in concentric or spiral tracks. The term is not intended to be limited to discs having the dimensions, track spacing, formatting, and feature sizes of commercial CD-ROM discs. The commercial CD-ROM format represents the presently known limit to the resolution of the CD-arrays of the present invention. The analogy to CD-ROM format is made for convenience, and to illustrate the magnitude of the advantage of the present invention over the current VLSIPS method. CD-arrays having synthesis sites on the order of ten to twenty microns in diameter (100 to 400 square microns in area), for example, are intended to be within the scope of the present invention. Such "low-density" embodiments of the invention will not be capable of displaying $10^9$ compounds, but they will require less precise and less sensitive equipment for their use. Less dense arrays will also be amenable to less complex formatting schemes, such as the use of polar coordinates in analogy to the X-Y coordinate system used in VLSIPS. The disc diameter may also vary widely, but is preferably from about one inch to about 12 inches.

By activating selected synthesis sites, and subsequently exposing the disc to a chemical monomer reagent A' capable of reacting with the activated synthesis sites, a chemical fragment A is attached to the selected sites. This fragment will usually carry a functional group, which will usually be masked by a laser-removable protecting group. The process of irradiating selected synthesis sites is repeated, and the disc is exposed to a second monomer reagent B', capable of reacting with activated synthesis sites to attach fragment B. Where these sites were previously selected for attachment of fragment A, reagent B' will covalently attach fragment B to the functional group of A. The cycles of irradiation and reaction are repeated, with the computer that controls the laser and disc rotation also maintaining a database of the irradiation and chemical exposure history of each synthesis site, until the desired library of compounds is assembled from the monomer reagents. The entire disc, or only selected synthesis sites, may then be irradiated to remove any remaining protecting groups The disc is then assayed to detect library members having some desirable property, such as the ability to bind selectively to an analyte. Bound analyte is optionally made more detectable to laser light with a visualization reagent or process, and synthesis sites carrying bound analyte are then detected by "reading" the disc with a laser, in a manner analogous to the reading of a CD-ROM.

The present invention is particularly suited to sequencing DNA by hybridization to arrays of oligonucleotides, as described for instance in U.S. Pat. No. 5,525,464, the contents of which are hereby incorporated by reference. In this embodiment of the present invention, fluorescently or otherwise labeled DNA fragments are allowed to hybridize to an array of oligonucleotide probes on a disc, and by identifying the probes to which the DNA has hybridized the sequence of the DNA may be deduced. As described in U.S. Pat. No. 5,525,464, one would ideally carry out hybridizations to all possible 11-mer oligonucleotide probes, but the technical difficulty of preparing such an array is acknowledged to be a limitation. The present invention removes this limitation, and makes possible for the first time the preparation of an array of all 4,194,304 11-mer oligonucleotides. Indeed, the present invention makes possible an array of all 16,777,216 possible 12-mers, which would reduce the number of target DNA fragments needed for sequencing a given gene or genome. Arrays of even longer oligonucleotides are possible (there are just over $10^9$ possible 15-mers), but end mismatches become difficult to distinguish as the oligonucleotide length increases.

DETAILED DESCRIPTION OF THE INVENTION

The array disc comprises a first layer, hereinafter referred to as the synthesis layer, and preferably incorporates a second layer, hereinafter referred to as the reflective layer, located below the synthesis layer. At least one additional layer will be present, for purposes of mechanical strength, for protection of a reflective layer or of the synthesis layer, and to constrain liquid reagents to the synthesis layer. The synthesis layer is initially functionalized with reactive groups, such as amino groups, which are blocked by a laser-removable protecting group. The materials of which the array disc is constructed are not critical, they may for example be metallic, polymeric, ceramic, vitreous, or composites thereof. The only requirements of the materials are that, where they are exposed to solvents and reagents during the synthesis of the library members, they be effectively insoluble in and inert to those solvents and reagents. The materials must also render the disc sufficiently rigid to avoid deformations that would prevent accurate irradiation of the synthesis sites. Where a reflective surface is separated from the synthesis surface by a layer of material, or where a transparent disc is employed, this material must also be transparent to the frequency of the laser used to assay the array, referred to herein as the interrogating laser.

Methods of preparing functionalized surfaces, including functionalized glass, metal, and polymer surfaces, are well known in the art. The functional groups may be attached to the surface by a spacer of any desirable length. The spacer may possess certain desirable properties, such as low non-specific binding to proteins or nucleic acids, as appropriate for the particular assay being contemplated by the practitioner. The spacer may be linear or branched, and may optionally carry a plurality of functional groups. The patents incorporated herein by reference disclose or reference exemplary methods to those skilled in the art. The fluorocarbon surface masking method disclosed in U.S. Pat. No. 5,474,796 may optionally be employed, wherein an initial laser ablation of a fluorocarbon layer is used to constrain the synthesis sites to pre-defined locations.

It will be appreciated by those skilled in the art that the disc will require formatting in some manner, in order to define tracks, sectors, frames, addresses, and other features. These features provide tracking error detection, frame sync signals, data addresses, and other information to the read-write device that enable accurate and reproducible writing and reading of data in a CD-ROM, and similar information will be required for reproducible and accurate irradiation and subsequent assaying of the CD-array. A variety of CD data formats are available, and the present invention contemplates the use of any of these formats, or other methods of locating a selected synthesis site.

Certain formatting features can be incorporated into the structure of the disc itself, for example by pressing, etching, or laser ablation, as is well-known in the art. These features are usually detectable by the writing and reading laser optics, but may be read and utilized by other components of the read-write device, such as a separate diode laser dedicated to tracking. The present invention anticipates that the disc may be spun with either constant linear velocity or constant angular velocity, at the discretion of the practitioner.

Other formatting features can be written by the "writing" laser in a formatting step prior to the initiation of library synthesis, in a manner analogous to the formatting of a hard disc drive. Synthesis sites activated in the formatting step will then be reacted with a "formatting reagent", in order to attach a formatting moiety that provides a detectable signal to the interrogating laser. The formatting moiety will be chosen to be resistant to removal by the chemical solvents and reagents subsequently used by the practitioner in the synthesis of the library. Detectability might be inherent to the formatting reagent, or might be introduced in subsequent operations that modify the formatting moiety. As examples of inherent detectability, if the library is to be assayed by attenuated reflectance, the formatting reagent may comprise one or more unreactive dye molecules absorbing the frequency of the interrogating laser. If the library is to be assayed by interferometry, the formatting reagent may comprise an unreactive polymer of sufficient size to provide a detectable change in phase of the interrogating laser light. As an example of introduced detectability, the formatting steps could comprise introducing biotin as the formatting moiety, followed by avidin binding to the biotin and silver staining of the avidin to opacify the biotinylated synthesis sites.

The reading of a CD-array for detection of binding of analyte will in some cases involve scanning a mostly "blank" disc for the occasional signal. It will be appreciated by those skilled in the art that the "eight to fourteen modulation" or EFM encoding characteristic of current audio and CD-ROM disc technology is not required in such cases, since binding of analyte to adjacent synthesis sites is unlikely. Thus, the present invention anticipates that the computer may have direct control of the writing mechanism during synthesis, and also may have direct access to the primary signal generated by the reading optics during the assay, bypassing much of the electronic circuitry present in conventional CD-ROM devices.

The term "light-directed synthesis" as used herein refers not only to photochemistry, but also to thermal reactions that are induced by laser irradiation, and catalyzed reactions where the catalyst is photo-generated. Reactions that either deprotect or create reactive functional groups are contemplated to be within this definition.

The deprotection (activation) of the synthesis layer and of the growing library members by presently available photochemical (as opposed to thermal) means would be impractical using the diode lasers available at the present time, since diode lasers are not currently capable of generating ultraviolet light of sufficient intensity to carry out photochemistry at an acceptable rate. Ultraviolet laser diodes of sufficient intensity would be ideal for the present application. Photochemical deprotection, therefore, is preferably accomplished at the present time by replacing the diode laser found in a commercial recordable CD-ROM device with a more powerful "bench top" laser, and delivering the laser beam to the disc write head by reflection or by means of fiber optics. U.S. Pat. No. 5,318,679 describes appropriate laser equipment for conducting photochemical deprotection for purposes of light-directed synthesis, and similar equipment is widely available from commercial sources. The laser will be chosen to provide a frequency of light appropriate for the particular photo-removable protecting groups being employed. With the laser being external to the CD-ROM device, the practitioner has the option of switching lasers, making it possible to employ a plurality of protecting groups. It will be understood that when reference is made herein to the "radial motion" of the laser, the expression refers to motion of the read-write head, which may or may not actually comprise a laser. The read-write head may comprise a lens at the end of an optical path, with the laser itself remaining stationary.

The size of the synthesis area will in most cases be determined by the degree to which the laser light is focused, which is dependent on the focal length of the lens through which the light is delivered and on the distance from the lens to the synthesis layer. The size of the synthesis sites can be varied to suit the resolution of the overall system and the number of library members to be prepared on the disc.

The intensity and duration of a laser pulse required for quantitative or near-quantitative deprotection or activation will be dependent on numerous factors: the power and frequency of the laser, the amount of power actually delivered to the synthesis sites by the system optics, the size of the synthesis site, and the photochemical properties of the protecting group chosen by the practitioner. Determination of the most effective power level and pulse length can be determined by known methods, for example those disclosed in U.S. Pat. No. 5,143,854, and is within the ability of one skilled in the relevant arts.

Alternatively, photo-removable protecting groups sensitive to the wavelengths available from current diode lasers would be advantageous. Such groups have not previously been reported, since there has been no need for them, but they could be designed by modification of the absorption maxima of known photoremovable protecting groups.

Some of the most effective currently employed photo-removable protecting groups, such as the nitroveratyloxy-carbonyl (NVOC) group, require a carbonyl group scavenger to be present in solution for optimum yields. Photo-removable silyl protecting groups, while not requiring a scavenger, nonetheless function more efficiently in a polar solvent. See V. N. R. Pillai, *Synthesis*, 1, (1980), incorporated herein by reference, for a general discussion of photo-removable protecting groups. See U.S. Pat. Nos. 5,486,633 and 5,489,678 (both incorporated herein by reference) for photo-removable protecting groups particularly useful for solid-phase synthesis of peptides and nucleic acids, and see U. Zehavi, *Adv. Carbohydrate Chem.* and *Biochem.*, 46, 179–204 (1988) for photo-removable protecting groups useful for carbohydrate synthesis.

Where such protecting groups and/or solvents are to be employed in the present invention, the CD-array structure will preferably incorporate an optically flat cover layer transparent to the wavelength of the activating laser, sealed at the circumference and at the inner annular edge, and will incorporate ports for introduction and withdrawal of reagent solutions. The synthesis layer, the seals, and the cover layer will define a disc-shaped space where reagent solutions may be maintained in contact with the synthesis layer during irradiation. An inner annular seal may optionally be a rotating seal, so that solutions might be pumped through the space under computer control without the need for removing the disc from the laser activation apparatus. The present invention also contemplates an alternative embodiment, in which a thin layer of solution or solvent is spin-cast onto the disk surface, using well-known technology developed for the preparation of thin films (See, e.g., C. W. Frank et al, *Science*, 273, 912–915, and references therein). Non-volatile solvents will be preferred. It will be appreciated that such designs also permit the automated introduction of monomer reagents and solvents.

It will be appreciated that the synthesis layer need not be rigid, but may comprise a covalently attached fluid or liquid crystal phase, such as a polyethylene glycol, or alternatively may comprise a gel phase with solvent molecules incorporated therein. Such solution-like phases are well known in the art, and are frequently used where polymer beads are employed as the support in solid-phase synthesis. In certain cases, such a phase is expected to obviate the need for a solvent space or layer.

It will be appreciated that the presence of a cover layer and/or solvent will effectively alter the focal length of the objective lens of the CD laser, and that the refractive index and thickness of these additional materials will have to be precisely controlled and/or monitored, and compensated for by the CD mechanism, if maximum resolution is to be maintained. Photo-removable protecting groups that do not require a liquid phase would be preferred in the present invention. Protecting groups that photo-fragment to volatile byproducts, for example, might be employed, with operations being conducted in a vacuum if required.

The deprotection of the functional groups may also be accomplished thermally by irradiation with conventional infrared lasers, for example the diode laser of a recordable CD-ROM device. Most rewritable CD-ROM devices rely on thermal effects to write data bits to the disc, using the localized heating induced by brief, highly focused irradiation. Momentary surface temperatures in excess of 300° C. are obtainable with such devices. U.S. Pat. No. 4,719,615 (incorporated herein by reference), together with the references therein, describes the technology and principles involved. Thermally removable protecting groups are known in the art; for example the t-butoxycarbonyl group (Boc group) decomposes to gaseous products at temperatures of about 180° C. (J. S. Zambounis et al., *Nature*, 388, 131–132 (1997); V. H. Rawal and M. P. Cava, *Tetrahedron Lett.*, 26, 6141 (1985); and H. H. Wasserman and G. D. Berger, *Tetrahedron*, 39, 2459 (1983)). It will be appreciated that where the thermal deprotection is not completed during a single irradiation period, multiple passes under the laser will eventually drive the reaction to the desired level of completeness, albeit at the cost of slowing down the overall process. Alternatively, the period of irradiation may be extended, however this will cause a larger area of the synthesis layer to be heated and deprotected, thereby reducing the achievable density of synthesis sites on the array. Partial deprotection at the margins of the synthesis site is to be expected, resulting in the synthesis of mixtures of compounds in the margin as the cycles accumulate. If the interrogating laser can selectively irradiate the central portions of the synthesis site, where deprotection is reliably complete at each cycle, this effect can be ignored. Alternatively, masking of the area around the synthesis sites by means of a fluorocarbon layer as described in U.S. Pat. No. 5,474,796 can eliminate marginally heated areas. It is anticipated that thermal reactions other than deprotection reactions will be inducible by the activating laser, for example acyl azides could be converted selectively to isocyanates as one step in a light-directed synthesis.

To initiate library synthesis, a pre-determined set of sites on a formatted CD-array disc is deprotected or otherwise activated by laser irradiation, and the array is then exposed to chemical reagents which attach the desired chemical moieties to the irradiated sites. The array is subjected to as many cycles of irradiation and chemical treatment as are desired. The computer may be used to schedule the processes, and is used to control the irradiation patterns and to store a record of the irradiation patterns and the chemical treatments that took place after each irradiation session. This record, or chronology, can be referred to later to enable the practitioner to deduce the structure of the library member at any given synthesis site. Alternatively, the entire chronology may be pre-determined by the practitioner, and employed as an instruction set by the computer.

As used herein, the term "spatial location" in reference to the location of a particular synthesis site or library member on the disc is equivalent to the "logical address" of the synthesis site, for purposes of associating bound analyte with the identity of the library member to which it has bound. The logical address is a locator which indicates a location on the disk with reference to formatting features, such as tracks, sectors, blocks, and the like. It will be appreciated that one need not know the actual physical locations of the library members on the CD-array disc in order to practice the present invention, unlike the prior art spatially addressable arrays that rely on x-y coordinates to encode compound identity.

The writing of a computer program capable of carrying out the tasks required by the present invention is within the ability of one skilled in the art of computer programming. The present invention contemplates that a variety of software designs will be applicable to the tasks of mapping the library onto the disc and directing the movements of the lasers, the CD-array disc, and optionally controlling reagent and solvent delivery to the CD-array.

After the desired number of irradiation and reaction cycles, the CD-array will usually be stripped of all remaining protecting groups. It will be appreciated that protecting groups not sensitive to removal by irradiation can be employed at any chemical reaction stage, so as to mask reactive functional groups that are desired to be present at a later stage of synthesis. Such groups may, for example, be removable by chemical or thermal means. Protecting groups that are photoremovable, but not sensitive to the wavelength of light being employed for the rest of the library synthesis, can be similarly employed. Such protecting groups will be utilized, for example, where a branched oligomer is the desired product, and the branching point requires activation after one or more rounds of irradiation.

The CD-array is then exposed to a substance of interest, under conditions that permit selective binding to those library members that have the greatest affinity for the substance. (The substance of interest, usually a protein, nucleic acid, or other biomolecule, is hereinafter referred to as the analyte.) Methods for effecting the selective binding of an analyte are well-known in the art, and are routinely employed in analytical procedures and when supported compound libraries are probed for binding affinity. Likewise, methods for the hybridization of nucleic acids to immobilized libraries of oligonucleotides are well-known, for example see U.S. Pat. No. 5,002,867, incorporated herein by reference.

In the pharmaceutical field, the analyte will usually be a protein, for example a receptor, an ion channel, an enzyme, or a signal transduction protein. In the genomics field, or in diagnostics or forensics, the library will often consist of nucleic acid sequences, or sequences of nucleic acid analogues such as peptide nucleic acids, and the property of interest will usually be the ability of library members to hybridize to single-stranded DNA or RNA. The ability of such libraries to bind DNA- or RNA-binding proteins, such as transcription activators or repressors, will also be of interest in the biochemical and pharmaceutical fields.

Typically, the array is exposed to a solution of the analyte of interest, under appropriate conditions to permit any selective binding or hybridization to occur. Unbound analyte is rinsed away, and any bound analyte is then optionally rendered more detectable to laser light with a visualization reagent or process as described below.

Finally, the present invention provides for the detection of analyte bound to individual library members of the CD-array. The CD-array is "read" in the same way that a conventional CD-ROM disc is read. See L. Boden, *Mastering CD-ROM Technology*, John Wiley & Sons (1995), ISBN 0-471-12174-6, (incorporated herein by reference) for an overview of the relevant techniques of encoding and decoding information in the CD format. Light from the interrogating laser passes through a synthesis site, is reflected from the reflective layer below the synthesis site, and is detected after reflection back through the synthesis site. In an alternative embodiment, there is no reflective layer and the laser light is detected after passing through the disc. The reading may be accomplished by detecting changes in some property of the laser light which has passed through the synthesis sites, said change being induced by the presence of the analyte or by the presence of a visualization reagent bound to or associated with the analyte. This change in property is detected by an appropriate detector, and converted to a digital signal, usually a binary signal, which is recorded by the computer. The property of the light altered by the analyte may be intensity, as is the case in presently available CD-ROM readers, but may be some other property such as polarization angle, wavelength, or phase.

In an alternative embodiment of the present invention, fluorescence of the analyte or of a fluorescent label bound to the analyte is induced by the laser and is detected by an appropriate device, for example a charge-coupled device (CCD) or a photocell. An example of the detection with laser light of fluorescently labeled analytes bound to a spatially adressable array is the "GeneArray" scanner, manufactured by Hewlett Packard (Palo Alto, Calif.). This device analyzes a centimeter-size, rectangular surface carrying an array of fluorescently labeled analyte DNA bound to an array of oligonucleotides. The array is held stationary and the laser beam is scanned across the surface. The present invention, by employing a rotating disc format rather than a stationary surface for the array of synthesis sites, makes it posible to carry out a similar operation over a far larger surface area. The "GeneArray" scanner is presently priced at well over $100,000, whereas first generation CD-ROM readers may presently be obtained for under $100.

In yet another embodiment, the interrogating laser beam may be linearly polarized, and the fluorescence polarization from a fluorescent label may then be detected. See M. E. Jolley, *J. Biomol. Screening*, 1, 33–38 (1996), and references therein, for a brief introduction to fluorescence polarization.

In one embodiment of the invention, the intensity of the light reflected from a synthesis site is noted by the computer. As the disc rotates, another synthesis site is brought into the laser beam, and the process is repeated. At any site where the analyte has bound to a library member, and where the site has been opacified to the laser beam by any of the methods described herein, the reflected signal is attenuated to a measurable degree. Scanning of the CD-array by laser reflectance therefore generates a signal whose intensity varies with the degree of opacification of each synthesis site. This signal is converted into a digital signal, which is processed by the computer. If the signal-to-noise ratio is sufficiently large, information about the relative degree of opacity, and hence about the relative binding affinity of the library member for the analyte, may be derived from the signal. A lower signal-to-noise ratio, on the other hand, might permit only a binary information signal (analyte bound/not bound) to be derived. The computer has access to the "chronology" of the array, which is a database containing the irradiative and chemical reaction history of each synthesis site in the array, and which defines the structure of the library member at each site. The computer can report this data for each synthesis site that has been rendered opaque, thereby correlating the structure with the binding of the analyte.

For detection based on such attenuation of the interrogating laser light, it will usually be necessary to modify the analyte so as to render it opaque to the laser beam. This may be accomplished by covalently attaching dye molecules to the analyte, such dye molecules being chosen to have a high absorption coefficient at the frequency of the laser. Preferably, large numbers of dye molecules are attached, for example by way of branched or dendrimeric linkers, so as to amplify the absorbance.

Alternatively, a visualizing or "opacifying" protocol might be employed wherein a reporter molecule with affinity for the analyte, for example an analyte-specific antibody, is allowed to bind to the analyte bound to the CD-array. Those skilled in the art will appreciate that there exists a wide variety of well-known methods for visualization of bound analytes with reporter molecules, for example antibody-based methods such as ELISA, various "sandwich" assays, and the use of biotin and avidin conjugates. The method chosen, whatever the details, will result in any synthesis sites that carry the analyte being rendered relatively opaque to the interrogating laser beam. For example, dye molecules that absorb the laser light might be attached to the reporting molecule, or to a visualization reagent that binds to the reporting molecule. Alternatively, an insoluble dye might be generated by an enzyme that is bound to the analyte, and the precipitated dye relied upon to attenuate the interrogating laser beam. Other approaches might employ colloidal gold particles, or a precipitated metal such as silver, to disperse the interrogating laser beam. An example of the use of metal particles can be found in *Angew. Chem. Int. Ed. Engl.*, 36, 1080 (1997), where nanoparticles of gold, platinum, and cadmium-selenium are employed to visualize photochemically deprotected synthesis sites with micron resolution. Colloidal particles may disperse or absorb light in a wavelength-dependent fashion.

These and other methods of selective opacification of sites carrying the analyte will be apparent to those skilled in the art. For an example of the use of attenuated reflectance to detect biomolecule binding, see Mandenius et al, *Anal. Biochem.*, 157, 283–288 (1986). The combination of reporter molecules, plus any attached or bound visualization reagents that render the analyte detectable, is collectively referred to herein as a label, and the overall process of attaching the label to the analyte is referred to as labeling.

Laser light passing through a layer of bound analyte will experience a change in phase, due to passage through the higher refractive index medium of the analyte, relative to light that has not passed through a layer of analyte. Such a change of phase can be detected by interferometry. For an example of interferometric detection of surface-bound biomolecules on a transmissive substrate, see U.S. Pat. No. 5,413,939, incorporated herein by reference. Suitable analyte labels for interferometric detection would present a long pathlength to the interrogating laser and/or a high refractive index. Suitable labels would, for example, comprise high-molecular weight polymer chains and high-refractive index materials such as halocarbons. Current CD-ROM and audio CD players, in fact, rely on interference effects to distinguish pits and lands on CD disks. For more recent examples of the reading of data on a reflective CD-ROM by means of interferometry, see U.S. Pat. No. 5,471,455, incorporated herein by reference. Although the present invention contemplates the use of a transmissive disc, a reflective disc is preferred because it enables the practitioner to more easily modify existing CD-ROM equipment for use in the present invention. Also, the reflective mode enhances signal strength because it entails passing the interrogating laser light twice through the synthesis sites, and through any detectable analyte attached thereto.

As described in the above-referenced patents, interferometry requires that the interrogating beam be split into a sample and a reference beam, and that the reference beam travel a path as nearly identical as possible to the sample beam, so that any phase change can be reliably ascribed to the presence of analyte. Generally, this requires that the reference beam be reflected from a location as physically close as possible to the synthesis site, to eliminate errors due to variations in the physical media. (Present audio and CD-ROM readers irradiate an area larger than the pit size, and use light reflected from the disc surface to either side of the information-containing track as the reference beam.) The formatting and/or track spacing of a CD-array disc intended for interferometric assay will thus have to allow adequate space near each synthesis site for the reference beam. It would also be advantageous to replicate every library member in such a way that repeating signals are generated from the spinning disc with a characteristic frequency, which facilitates the filtering of noise from the signal, as discussed in U.S. Pat. No. 5,413,939 referenced above.

Although the analytes of interest are likely to be optically active, and thus capable of inducing rotation in a reflected beam of polarized light, the amount of rotation induced directly by these analytes is expected to be insufficient for detection in most cases. It is anticipated, however, that "super-rotating" moieties, such as optically active helicenes, would provide effective visualizing reagents if attached at high enough density to the analyte. Alternatively, the very presence of a layer of analyte alters the polarization state of reflected light, and thus ellipsometry might be relied upon to detect the presence of analyte, as disclosed by C. F. Mandenius et al, *Anal. Biochem.*, 137, 106–114 (1984) and references therein. Data detection by measurement of small changes in the rotation of polarized light is currently employed in some commercial recordable CD-ROM systems. Representative examples may be found in U.S. Pat. No. 5,457,582 (incorporated herein by reference) and references therein.

U.S. Pat. No. 5,453,969 (incorporated herein by reference) discloses the use of conoscopic holography to read data from an optical disc, wherein the angular spectrum of reflected polarized light contains the desired information. A birefringent crystal rotates the polarization of the reflected light as a function of the angular spectrum, and a polarizer/analyzer then projects an image of the beam which exhibits fringes. The spacing of the fringes is a function of the angular spectrum, hence detection of the fringe pattern constitutes recovery of the original data. Given that a layer of attached analyte will alter the angular spectrum of reflected polarized light (Mandenius et al, *Anal. Biochem.*, 157, 283–288 (1986), referenced above, employed polarized light in their reflectance assay), a detector employing conoscopic holography should also provide a suitable means of assaying the CD-array.

It will be appreciated that the method of assay provided by the present invention does not require that the CD-array be prepared by laser-directed synthesis. For example, mass production of multiple copies of a CD-array, as might be desirable with a CD-array of bound oligonucleic acids intended for sequencing by hybridization, might be more economically achieved by another method, such as photolithography or microprinting.

It is intended that all patents and publications referred to in this disclosure are incorporated by reference, whether or not explicitly so indicated in the text.

SUMMARY

The present invention is a novel approach to the preparation and screening of large compound arrays. There are two notable features of the present invention which provide significant advantages over prior art methods:

(1) It relies largely on existing chemical methods, such as light-directed synthesis of compound arrays, and may utilize existing technology, such as commercial CD-ROM hardware, with only a moderate degree of modification. The present invention does not require the practitioner to invest in expensive equipment.

(2) The novel employment of a spinning disc for the substrate, in place of the linearly translated or scanned rectangular substrates of the prior art, greatly increases the surface area that can be accurately and reproducibly addressed with a laser. This makes possible an order-of-magnitude increase in the number of compounds that can be prepared and screened in a convenient and economic manner.

INDUSTRIAL UTILITY

The present invention may be employed for the synthesis and assay of oligonucleotide arrays, or arrays of oligonucleotide analogues such as peptide nucleic acids. These arrays have utility in diagnostics, forensics, and in gene mapping and sequencing. See, for example, E. Pennisi, Science, 272, 1736–1738 (1996); D. J. Lockhart et al., Nature Biotechnology, 14, 1675–1680 (1996); M. Chee et al., Science, 274, 610–614 (1996); and A. Goffeau, Nature, 385, 202–203. It may also be employed for the synthesis of peptides, arrays of which have utility for antibody profiling, diagnostics, and screening for pharmaceutical activity. Another utility of the present invention is the synthesis and screening of libraries of small (molecular weight≦700) organic molecules by light-directed solid-phase organic synthesis. The present invention is particulary suited to the synthesis and assay of carbohydrate libraries, which can be extremely large due to the positional and stereochemical isomerism available to oligosaccharides (e.g., there are over 8.3 million tetrasaccharides derivable from the eight hexose monomers). Modifications and other applications of the present invention, which are apparent to those skilled in the fields of chemistry, biology, and the pharmaceutical sciences, are considered to be part of and within the scope of the present invention.

What I claim is:

1. A method conducting an optical inspection of an array of synthesis sites to identify one or more synthesis sites where an analyte is bound, said method comprising the steps of:

providing a mechanism comprising a laser and laser detector;

providing an optical disc which includes encoded information in a form that is readable by the mechanism, said optical disc further including an array of synthesis sites where each of said synthesis sites includes chemically reactive, reactive compounds which are capable of binding selectively to an analyte and wherein said mechanism provides a laser beam which is used to optically inspect said synthesis sites and includes a sample beam and a reference beam and where said sample beam is reflected from or transmitted through said synthesis site and said reference beam is reflected from or transmitted through a location on said disc adjacent to said synthesis site;

using said mechanism to conduct an optical inspection of said array of synthesis sites to provide identification of which synthesis sites contain said analyte;

reading said encoded information with said mechanism and conducting said optical inspection in response to encoded information that was read.

2. A method of conducting an optical inspection of an array of synthesis sites to identify one or more synthesis sites where an analyte is bound, said method comprising the steps of:

providing a mechanism comprising a laser and a laser detector;

providing an optical disc which includes encoded information in a form that is readable by the mechanism, said optical disc further including an array of synthesis sites and a reflective surface located below said synthesis sites and where each of said synthesis sites includes chemically reactive, activated compounds which are capable of binding selectively to an analyte, and wherein said mechanism provides a laser beam which is used to optically inspect said synthesis sites;

using said mechanism to conduct an optical inspection of said array of synthesis sites to provide identification of which synthesis sites contain said analyte where said optical inspection includes the steps of: directing said laser beam through said synthesis site to provide an altered laser beam which contacts said reflective surface; reflecting said altered laser beam back from said reflective surface through said synthesis site to form a reflected signal beam; and detecting one or more properties of said reflected signal beam;

reading said encoded information with said mechanism and conducting said optical inspection in response to encoded information that was read.

3. A method of conducting an optical inspection of an array of synthesis sites to identify one or more synthesis sites where an analyte is bound, said method comprising the steps of:

providing a mechanism comprising a laser and a laser detector;

providing an optical disc which includes encoded information in a form that is readable by the mechanism, said optical disc further including an array of synthesis sites where each of said synthesis sites includes chemically reactive, activated compounds which are capable of binding selectively to an analyte and wherein said mechanism provides a laser beam which is used to optically inspect said synthesis sites;

using said mechanism to conduct an optical inspection of said array of synthesis sites to provide identification of which synthesis sites contain said analyte, wherein said optical inspection includes, the steps of directing said laser beam through said synthesis site to provide an altered laser beam which is transmitted through said synthesis site and detecting one or more properties of said altered laser beam which has been transmitted through said synthesis site;

reading said encoded information with said mechanism and conducting said optical inspection in response to encoded information that was read.

4. The method of conducting an optical inspection of an array of synthesis sites according to anyone of claims 1 through 3 wherein said analyte includes a polypeptide, protein, nucleic acid or oligonucleotide.

5. The method according to any one of claims 1 through 3 which includes the additional step of using said mechanism to conduct light-directed synthesis in at least a portion of at said synthesis sites.

6. The method of conducting an optical inspection of an array of synthesis sites according to any one of claims 1 through 3 wherein each of said synthesis sites covers an area on said optical disc of between 100 and 400 square microns.

7. The method of conducting and optical inspection of an array of synthesis sites according to any one of claims 1 through 3 wherein said analyte includes a label selected from the group of fluorescent labels, metal labels and dye labels.

8. The method of conducting an optical inspection of an array of synthesis sites according to any one of claims 1 through 3 wherein said analyte is capable of altering one or more properties of said laser beam, said properties being selected from the group of intensity, polarization angle, wavelength and phase.

9. A method of detecting the presence of an analyte, comprising the steps of:

providing a mechanism comprising a laser and a laser detector;

providing an optical disc with encoded information in a form that is readable by the mechanism and an array of synthesis sites wherein each of said sites includes chemically reactive, activated compounds which are capable of binding selectively to an analyte, said mechanism including a laser beam capable of synthesis and optical inspection of said sites;

exposing at least some of the array of synthesis sites to a substance of interest, wherein said substance of interest may comprise an analyte;

conducting an optical inspection of said sites using said mechanism, to inspect them for the binding of selected analytes to said synthesis sites;

reading said encoded information with said mechanism and conducting said optical inspection in response to encoded information that was read.

* * * * *

UNITED STATES PATENT AND TRADEMARK OFFICE
CERTIFICATE OF CORRECTION

PATENT NO. : 7,094,609 B2
APPLICATION NO. : 09/269092
DATED : August 22, 2006
INVENTOR(S) : James Paul Demers Page 1 of 3

It is certified that error appears in the above-identified patent and that said Letters Patent is hereby corrected as shown below:

On the first page, column 1 (Title), line 3, please delete "DISK" and insert -- DISC -- therefor.

On the first page, column 2 (Other Publications), line 4, please delete "H1183;" and insert -- H1183, -- , therefor.

On the first page, column 2 (Other Publications), line 9, please delete "Biotrechnology," and insert -- Biotechnology, -- , therefor.

On the first page, column 2 (Other Publications), line 28, please delete "1991)." and insert -- 1996). --, therefor.

On the first page, column 2 (Attorney, Agent, or Firm), line 2, after "LLP" insert -- . -- .

On page 2, column 1 (U.S. Patent Documents), line 41, after "5,795,716 A 8/1998" please delete "Chee" and insert -- Chee et al. --, therefor.

On page 2, column 1 (U.S. Patent Documents), line 65, after "2002/0097658 A1 7/2002" delete "Worthington" and insert -- Worthington et al. --, therefor.

On page 2, column 2 (Other Publications), line 15, please delete "Detectin" and insert -- Detection --, therefor.

On page 2, column 2 (Other Publications), line 16, please delete "Porteases" and insert -- Proteases --, therefor.

On page 2, column 2 (Other Publications), line 21, please delete ""Deconvoluation" and insert -- "Deconvolution -- , therefor.

UNITED STATES PATENT AND TRADEMARK OFFICE
CERTIFICATE OF CORRECTION

PATENT NO. : 7,094,609 B2
APPLICATION NO. : 09/269092
DATED : August 22, 2006
INVENTOR(S) : James Paul Demers It is certified that error appears in the above-identified patent and that said Letters Patent is hereby corrected as shown below:

On page 2, column 2 (Other Publications), line 31, please delete ""interaction" and insert -- "The interaction --, therefor.

On page 2, column 2 (Other Publications), line 48, please delete "Pyrrholes,"" and insert -- Pyrroles," --, therefor.

On page 2, column 2 (Other Publications), line 55, please delete "and" and insert -- of --, therefor.

At column 1, line 3, please delete "DISK" and insert -- DISC --, therefor.

At column 1, line 7, after "60/026,415" insert --, --.

At column 2, line 64, delete "oligonuceotide" and insert -- oligonucleotide --, therefor.

At column 4, line 45 (approx.), after "groups" insert -- . --.

At column 5, lines 36-37 (approx.), please delete "well known" and insert

-- well-known --, therefor.

At column 7, line 35-36, please delete "nitroveratyloxycarbonyl" and insert

-- nitroveratryloxycarbonyl --, therefor.

At column 7, line 65, please delete "et al," and insert -- et al., --, therefor.

At column 8, line 7, please delete "well known" and insert -- well-known --, therefor.

At column 10, line 37, please delete "adressable" and insert -- addressable --, therefor.

At column 10, line 44 (approx.), please delete "posible" and insert -- possible --, therefor.

At column 11, line 50, please delete "et al," and insert -- et al., --, therefor.

UNITED STATES PATENT AND TRADEMARK OFFICE
CERTIFICATE OF CORRECTION

PATENT NO. : 7,094,609 B2
APPLICATION NO. : 09/269092
DATED : August 22, 2006
INVENTOR(S) : James Paul Demers It is certified that error appears in the above-identified patent and that said Letters Patent is hereby corrected as shown below:

At column 12, line 45, please delete "et al," and insert -- et al., --, therefor.

At column 12, line 63, please delete "et al," and insert -- et al., --, therefor.

At column 13, line 48 (approx.) please delete "particulary" and insert -- particularly --, therefor.

At column 14, line 3, in Claim 1, after "reactive," delete "reactive" and insert -- activated --, therefor.

At column 14, line 67, in Claim 3, delete "includes," and insert -- includes --, therefor.

At column 15, line 22 (approx.), in Claim 7, delete "and" and insert -- an --, therefor.

Signed and Sealed this

Eighteenth Day of December, 2007

JON W. DUDAS
*Director of the United States Patent and Trademark Office*